United States Patent
Morikawa et al.

(10) Patent No.: US 12,427,178 B2
(45) Date of Patent: Sep. 30, 2025

(54) COMPOSITION FOR MAINTAINING OR IMPROVING ORAL IMMUNE FUNCTION

(71) Applicant: TOYO SHINYAKU CO., LTD., Fukuoka (JP)

(72) Inventors: Takumi Morikawa, Saga (JP); Takashi Iwamoto, Saga (JP); Makoto Suzuki, Saga (JP); Shinichiro Takashima, Saga (JP); Tomoyasu Kamiya, Saga (JP)

(73) Assignee: TOYO SHINYAKU CO., LTD., Fukuoka (JP)

( * ) Notice: Subject to any disclaimer, the term of this patent is extended or adjusted under 35 U.S.C. 154(b) by 487 days.

(21) Appl. No.: 17/909,881

(22) PCT Filed: Mar. 24, 2022

(86) PCT No.: PCT/JP2022/013812
§ 371 (c)(1),
(2) Date: Sep. 7, 2022

(87) PCT Pub. No.: WO2022/210232
PCT Pub. Date: Oct. 6, 2022

(65) Prior Publication Data
US 2023/0190855 A1   Jun. 22, 2023

(30) Foreign Application Priority Data
Mar. 31, 2021  (JP) .................. 2021-059529

(51) Int. Cl.
*A61K 36/00* (2006.01)
*A61K 36/8998* (2006.01)
*A61P 37/02* (2006.01)

(52) U.S. Cl.
CPC .......... *A61K 36/8998* (2013.01); *A61P 37/02* (2018.01)

(58) Field of Classification Search
CPC .................. A61P 37/02; A61K 36/8998
See application file for complete search history.

(56) References Cited

FOREIGN PATENT DOCUMENTS

| JP | 2001-314170 A | 11/2001 |
| JP | 2003-339349 A | 12/2003 |
| JP | 2009-143851 A | 7/2009 |
| JP | 2011-184300 A | 9/2011 |
| JP | 2016193882 A | * 11/2016 |
| JP | 2017-039658 A | 2/2017 |

OTHER PUBLICATIONS

ISR for PCT/JP2022/013812, dated May 17, 2022.
Akahoshi et al., "Effects of Continuous Intake of Green Juice from Young Barley Leaves on Human Salivary IgA", Abstracts of Presentation, The 2003 Annual Conference of the Japan Society for Bioscience, Biotechnology and Agrochemistry, p. 223 (2003) (w/ translation) [cited in ISR].
"Recommended Aojiru for colds", Why Aojiru is Effective in Preventing Colds (Online) (2019), retrieved from https://web.archive.org/web/20190619204217/https://aojiru-sensei.com (w/ translation) [cited in ISR].
Radke et al., "Starter formula enriched in prebiotics and probiotics ensures normal growth of infants and promotes gut health: a randomized clinical trial", Pediatric Research, 81(4):622-631 (2017).

\* cited by examiner

*Primary Examiner* — Qiuwen Mi
(74) *Attorney, Agent, or Firm* — Greenblum & Bernstein, P.L.C.

(57) ABSTRACT

It is a composition comprising young barley grass, used for promoting salivary IgA secretion, maintaining or improving oral immune function, or mucosal immune function, or preventing or alleviating upper airway infection.

1 Claim, No Drawings

COMPOSITION FOR MAINTAINING OR IMPROVING ORAL IMMUNE FUNCTION

TECHNICAL FIELD

The present invention relates to a composition that maintains and improves oral immune function, specifically to a composition for maintaining or improving oral immune function comprising young barley grass.

BACKGROUND ART

Recently, against the background of the increase in interest on health, various health food products are developed, and various materials used in health food products are investigated.

Among these, young barley grass is used as material for health food products or green juice, and its functionality such as anti-cholesterol effect is widely investigated (for example, patent document 1).

CITATION LIST

Patent Literature

Patent document 1: Japanese Laid Open Patent Publication No. 2001-314170

SUMMARY OF INVENTION

Technical Problem

The object of the present invention is to provide a composition having a new function using young barley grass.

Solution to Problem

The present inventors made a keen study on the function of young barley grass, and they found out that young barley grass promotes secretion of IgA in saliva, and exerts an excellent oral immune function, mucosal immune function, or function of preventing or alleviating upper airway infection. The present invention has been thus completed.

Specifically, the present invention is as follows.

[1] A composition for maintaining or improving oral immune function, comprising young barley grass.
[2] A composition for maintaining or improving mucosal immune function, comprising young barley grass.
[3] A composition for promoting salivary IgA secretion, comprising young barley grass.
[4] A composition for preventing or alleviating upper airway infection, comprising young barley grass.
[5] A composition for maintaining or improving oral immune function, comprising dietary fiber derived from young barley grass, as active ingredient.
[6] A composition for maintaining or improving mucosal immune function, comprising dietary fiber derived from young barley grass, as active ingredient.
[7] A composition for promoting salivary IgA secretion, comprising dietary fiber derived from young barley grass, as active ingredient.
[8] A composition for preventing or alleviating upper airway infection, comprising dietary fiber derived from young barley grass, as active ingredient.

Advantageous Effects of Invention

The composition of the prevent invention can increase IgA level in saliva, and can maintain or improve oral immune function or mucosal immune function, or prevent or alleviate upper airway infection.

DESCRIPTION OF EMBODIMENTS

The composition of the present invention is characterized by comprising young barley grass.

Since the composition of the present invention can increase IgA in saliva, by orally intaking the composition continuously and routinely, it is possible to maintain or improve immune function of oral cavity or mucosal membrane. Here, maintain or improve oral immune function in the present invention is a concept comprising suppressing decrease (maintaining) oral immune function, and/or improving (ameliorating) oral immune function. Further, maintain or improve mucosal immune function is a concept comprising suppressing decrease (maintaining) mucosal immune function, and/or improving (ameliorating) mucosal immune function.

Further, the composition of the present invention can prevent or alleviate (ameliorate) upper airway infection (flu symptoms) by orally intaking the composition continuously and routinely to thereby maintain or improve oral immune function. Upper airway infection means that flu viruses, etc. infect airway mucosa from oral cavity or nasal cavity, the viruses proliferate in these sites, and symptoms such as sneeze, snivel, nasal congestion, throat pain, etc. appear.

(Salivary IgA)

IgA means immunoglobulin A, and is a type of immunoglobulin present in mammals and birds, etc. There are five types of immunoglobulins, IgG, IgA, IgM, IgD, and IgE, and they differ in their production mechanism, function, role, acting site or period, etc.

For example, regarding IgA and IgG, as cytokines generated when Tfh cells induce classswitch from IgM are different, secretion of IgA and secretion of IgG are controlled differently. Specifically, increase of IgA level and increase of IgG level occur due to different mechanisms. Further, while IgA plays a primary role in the mucosal immune system, IgG plays a primary role in the whole-body immune system. Therefore, IgA and IgG differ from their secretion mechanism to their roles.

Further, the role of IgA differs depending on the site being secreted. For example, IgA in stool is thought to be associated with gut immunity, while IgA in saliva is associated with oral immunity, and stool IgA and salivary IgA differ in their roles.

Further, for IgA, against invasion of the same antigen, there are tissues where IgA is secreted, and not secreted. That is, even if the IgA secretion level of a particular tissue is increased, it does not mean that IgA secretion level of other tissues is also increased. For example, when intaking a certain substance, even if stool IgA level increases, salivary IgA does not necessarily increase. (see Pediatric RESEARCH, volume 81, number 4, p. 622-631). In this reference, it is described that in an infant having intake a predetermined milk, stool IgA level has increased, while salivary IgA level did not increase. Specifically, in the column "Immune Measurements" in page 627, it is described that stool IgA concentrations were significantly higher in the Test group compared with the Control group at both 3 and 6 months, while salivary IgA concentrations were not significantly different between the Test groups. As such, secretion of salivary IgA and secretion of stool IgA do not necessarily occur at the same time.

(Young Barley Grass)

Barley (*Hordeum vulgare* L.) is said to be native of Central Asia, is a poaceous annual or biennial grass plant, and is broadly divided into two-row barley, six-row barley, etc. from their spike form. Barley comprises barley β-glucan which is a water soluble dietary fiber, and non-soluble dietary fiber in abundance. Young barley grass used in the composition of the present invention is not particularly limited as long as it is one that is commonly available, and any type of young barley grass such as two-row barley, six-row barley, etc. can be used. Further, it can comprise stem together with young leaves.

As for young barley grass, for example, ground product, juice, extract, etc. can be used. As for ground product, dried powder (young barley grass powder), finely divided powder and its dried product (dried finely divided powder), etc. can be exemplified. Juice or extract can be in liquid form, but can be also used in paste form or as dried powder (juice powder, extract powder). Extract can be obtained by extracting using an appropriate solvent, and examples of solvents include water (warm water, hot water), ethanol, and water-containing ethanol. In the present invention, since it comprises more dietary fiber, and can further enjoy the effect of the present invention, ground product is preferable, and among ground products, dried powder (young barley grass powder) is particularly preferable.

Further, from the viewpoint that young barley grass used in the present invention can further enjoy the effect of the present invention, it is preferable to comprise 20% by mass or more of dietary fiber, more preferably to comprise 25% by mass or more, and further preferably to comprise 30% by mass or more. The upper limit can be for example 70% by mass.

(Composition of the Present Invention)

The composition of the present invention can be used for example, as medicine (including quasi-drug), or as so-called health food products such as functional foods which indication of efficacy is allowed from a prescribed authority, including foods for specified health use, foods with nutrient function claims, foods with function claims, or the like.

The composition for maintaining or improving oral immune function of the present invention is not particularly limited as long as it can be distinguished from other products as product, in the point of comprising young barley grass and of being used for maintaining and/or improving (ameliorating) oral immune function, and for example those with an indication of having a function of maintaining and/or improving (ameliorating) oral immune function on any of the main body, package, instructions, advertisement (advertising medium) of the product of the present invention are encompassed in the scope of the present invention. The composition for maintaining or improving oral immune function of the present invention can be one indicating young barley grass or ingredients derived from young barley grass (dietary fiber derived from young barley grass, etc.) as active ingredients, but is not limited to those with an indication of comprising young barley grass or ingredients derived from young barley grass (dietary fiber derived from young barley grass, etc.) as active ingredients on the package of the product, etc. For example, it can be one not specifying the active ingredients. Further, even it is a general food product, those manufactured and sold by suggesting the use are encompassed in the scope of the present invention. For example, food products etc. sold by posting a personal experience referring to maintenance or improvement of immune function of the oral cavity (oral mucosa) as a personal impression of an individual having intake the product, on the website, etc. are also encompassed in the scope of the invention. Further, foods with function claims using articles, etc. showing maintenance and/or improvement of oral immune function as a scientific basis, and which functional substance is young barley grass or ingredients derived from young barley grass, and which function related to maintenance and/or improvement of the immune function is the submitted claim are encompassed in the scope of the present invention.

Specifically, in a so-called health foods, those indicating "help to maintain oral immune function in a healthy individual", "boosting immunity of the oral cavity", "increasing immunity of the oral cavity", "enhancing immunity of the oral cavity", "supporting oral immunity", "maintaining protection in the oral cavity", "boosting protection in the oral cavity", "increasing protection in the oral cavity", "enhancing protection in the oral cavity", etc. can be exemplified. Further, "help to maintain immune function of oral mucosa in a healthy individual", "boosting immunity of oral mucosa", "increasing immunity of oral mucosa", "enhancing immunity of oral mucosa", "supporting oral mucosa immunity", "maintaining protection of oral mucosa", "boosting protection of oral mucosa", "increasing protection of oral mucosa", "enhancing protection of oral mucosa" etc. can be exemplified.

The composition for maintaining or improving mucosal immune function of the present invention is not particularly limited as long as it can be distinguished from other products as product, in the point of comprising young barley grass and of being used for maintaining and/or improving (ameliorating) mucosal immune function, and for example those with an indication of having a function of maintaining and/or improving (ameliorating) mucosal immunity on any of the main body, package, instructions, advertisement (advertising medium) of the product of the present invention are encompassed in the scope of the present invention. The composition for maintaining or improving mucosal immune function of the present invention can be one indicating young barley grass or ingredients derived from young barley grass (dietary fiber derived from young barley grass, etc.) as active ingredients, but is not limited to those with an indication of comprising young barley grass or ingredients derived from young barley grass (dietary fiber derived from young barley grass, etc.) as active ingredients on the package of the product, etc. For example, it can be one not specifying the active ingredients. Further, even it is a general food product, those manufactured and sold by suggesting the use are encompassed in the scope of the present invention. For example, food products sold by posting a personal experience referring to maintenance or improvement (amelioration) of mucosal immunity as a personal impression of an individual having intake the product, on the website, etc. are also encompassed in the scope of the invention. Further, foods with function claims using articles, etc. showing maintenance and/or improvement (amelioration) of mucosal immunity as a scientific basis, and which functional substance is young barley grass or ingredients derived from young barley grass, and which function related to maintenance and/or improvement of the immune function is the submitted claim are encompassed in the scope of the present invention.

Specifically, in so-called health foods, those indicating "help to maintain mucosal immunity in a healthy individual", "boosting mucosal immunity", "increasing mucosal immunity", "enhancing mucosal immunity", "supporting mucosal immunity", "maintaining protection of the mucosa", "boosting protection of the mucosa", "increasing protection of the mucosa", "enhancing protection of the mucosa", etc. can be exemplified.

The composition for preventing or alleviating upper airway infection of the present invention is not particularly limited as long as it can be distinguished from other products as product, in the point of comprising young barley grass and of being used for preventing or alleviating (ameliorating) upper airway infection, and for example those with an indication of having a function of preventing upper airway infection (flu symptoms) on any of the main body, package, instructions, advertisement (advertising medium) of the product of the present invention are encompassed in the scope of the present invention. The composition for preventing or alleviating upper airway infection of the present invention can be one indicating young barley grass or ingredients derived from young barley grass (dietary fiber derived from young barley grass, etc.) as active ingredients, but is not limited to those with an indication of comprising young barley grass or ingredients derived from young barley grass (dietary fiber derived from young barley grass, etc.) as active ingredients on the package of the product, etc. For example, it can be one not specifying the active ingredients. Further, even it is a general food product, those manufactured and sold by suggesting the use are encompassed in the scope of the present invention. For example, food products sold by posting a personal experience referring to prevention of upper airway infection (flu symptoms) as a personal impression of an individual having intake the product, on the website, etc. are also encompassed in the scope of the invention. Further, foods with function claims using articles, etc. showing prevention of upper airway infection (flu symptoms) as a scientific basis, and which functional substance is young barley grass or ingredients derived from young barley grass, and which function related to maintenance and/or improvement of the immune function is the submitted claim are encompassed in the scope of the present invention.

Specifically, in so-called health foods, those indicating "preventing onset of upper airway infection", "preventing onset of flu", "preventing flu", "less prone to flu", etc. can be exemplified.

The composition for promoting salivary IgA secretion of the present invention is not particularly limited as long as it can be distinguished from other products as product, in the point of comprising young barley grass and of being used for promoting secretion of IgA in saliva, and for example those with an indication of having a function of promoting secretion of IgA in saliva on any of the main body, package, instructions, advertisement (advertising medium) of the product of the present invention are encompassed in the scope of the present invention. The composition for promoting salivary IgA secretion of the present invention can be one indicating young barley grass or ingredients derived from young barley grass (dietary fiber derived from young barley grass, etc.) as active ingredients, but is not limited to those with an indication of comprising young barley grass or ingredients derived from young barley grass (dietary fiber derived from young barley grass, etc.) as active ingredients on the package of the product, etc. For example, it can be one not specifying the active ingredients. Further, even it is a general food product, those manufactured and sold by suggesting the use are encompassed in the scope of the present invention. For example, food products sold by posting a personal experience referring to promotion of secretion of IgA in saliva as a personal impression of an individual having intake the product, on the website, etc. or the like are also encompassed in the scope of the invention.

Specifically, in so-called health foods, those indicating "promoting secretion of IgA in saliva", "boosting IgA level in saliva", "promoting IgA secretion in the oral cavity", "boosting IgA level in the oral cavity" etc. can be exemplified.

Examples of the form of the composition of the present invention include, for example, tablet form, capsule form, powder form, granule form, liquid form, grain form, bar form, plate form, block form, solid form, pellet form, paste form, cream form, caplet form, gel form, chewable tablet form, stick form, or the like. It can be in form of ice cream, jelly, cookies, cake, chocolate, PET bottle beverage, etc. Among these, the form of tablet form, capsule form, powder form, granule form, pellet form, chewable tablet form is preferable, and powder form and granule form are particularly preferable.

In case the composition of the present invention is made into a tablet form, pellet form, chewable tablet form, it is preferable to add one or more of any of excipient, lubricant, or fluidizer. As such, the molding property is enhanced, and the storage stability of the produced agent is improved. Particularly, by using an excipient and lubricant, the storage stability can be further improved.

As for the content of young barley grass in the composition of the present invention, it can be comprised within the scope with which the effect is exerted. For example, in the composition of the present invention, in dry mass equivalent, young barley grass can be comprised in an amount of 0.01 to 100% by mass, and it is preferable to be comprised in an amount of 0.1 to 100% by mass, more preferable to be comprised in an amount of 1 to 100% by mass.

As for the content of dietary fiber derived from young barley grass in the composition of the present invention, it can be comprised within the scope with which the effect is exerted. For example, in the composition of the present invention, in dry mass equivalent, dietary fiber derived from young barley grass can be comprised in an amount of 0.01 to 80% by mass, and it is preferable to be comprised in an amount of 0.1 to 75% by mass, more preferable to be comprised in an amount of 1 to 70% by mass.

The amount of intake of young barley grass in the present invention is not particularly limited. However, to further enjoy the effect more effectively, it is preferable to intake so that the amount of intake of young barley grass of an adult per day is 0.25 g or more, more preferable to intake so that it is 0.5 g or more, and further preferable to intake so that it is 1.0 g or more. The upper limit is for example 30 g, preferably 20 g, and more preferably 10 g.

Further, the amount of intake of dietary fiber derived from young barley grass in the present invention is not particularly limited. However, to further enjoy the effect more effectively, it is preferable to intake so that the amount of intake of dietary fiber derived from young barley grass of an adult per day is 0.125 g or more, more preferable to intake so that it is 0.25 g or more, and further preferable to intake so that it is 0.5 g or more. The upper limit is for example 15 g, preferably 10 g, and more preferably 5 g.

The composition of the present invention can be appropriately designed so that the amount of intake per day of young barley grass or dietary fiber derived from young barley grass becomes the above-mentioned amount of intake, and it can be an embodiment to be taken at once, or an embodiment to be taken in plural times. For example, it can be stored as an amount per day in one container, or for example in plural containers of two to four.

The composition of the present invention can be produced by known methods, by adding ingredients other than young barley grass, according to need.

EXAMPLES

In the following, the present invention will be explained in further details by the Examples. However, the present invention is not limited to these Examples.

Example 1

The influence of intaking young barley grass on the salivary IgA concentration has been investigated and confirmed.

<Test Methods>

The test was performed by allowing 18 healthy adults to intake young barley grass for 2 weeks. Specifically, test was performed by dividing the test subjects into two groups, a group intaking 1.5 g of young barley grass powder per day (1.5 g group) and a group intaking 1.7 g per day (1.7 g group). The total dietary fiber amount in young barley grass was 46.7% for both groups. Intake of young barley grass was as follows: powder of young barley grass (young barley grass powder) was dissolved into a defined amount (100 mL) of water or hot water once a day, to be intake at dinner time.

<Measurement of Salivary IgA Concentration>

The test subjects were measured for salivary IgA concentration, before intake and 2 weeks after initiating intake. Specifically, measurement of salivary IgA concentration was made by using CUBE Reader (manufactured by SOMA), according to the usage of the device. First, a predetermined cotton swab was put on the tongue of the test subject, and it was continued to collect saliva until the cotton swab became blue. Then, the cotton swab was immersed into a buffer solution by stirring for 2 minutes. Three drops of the obtained buffer solution were dropped on a predetermined plate. The plated on which the buffer solution was dropped was set in the device, allowed to stand for 10 minutes, and the measurement value displayed on the device was read to store the data. The measurement was repeated twice for the same specimen, and the mean value was used as a measurement value.

Based on the measurement value, the change rate of salivary IgA concentration was calculated by the following formula.

$$\text{Change rate of salivary } IgA \text{ concentration} = \frac{\text{Measurement value of salivary } IgA \text{ concentration two weeks after initiation of intake}}{\text{Measurement value of salivary } IgA \text{ concentration before intake}} \times 100 \quad \text{[Expression 1]}$$

Change rate of salivary IgA concentration are shown in Table 1.

TABLE 1

| | Change rate (%) | |
|---|---|---|
| | Before intake | Two weeks after |
| Young barley grass 1.5 g | 100% | 188.3% |
| Young barley grass 1.7 g | 100% | 235.8% |

As shown in Table 1, by intaking young barley grass, a large increase of salivary IgA concentration was observed. Specifically, it has been elucidated that by the intake of young barley grass, secretion of salivary IgA could be promoted.

Therefore, according to the composition comprising young barley grass of the present invention, the immune function of the oral cavity (oral mucosa) can be improved, and further as salivary IgA prevents invasion of viruses, etc., upper airway infection can be prevented or alleviated.

Example 2

(Production of Powder Beverage)

Powder beverage consisting of the following ingredients was produced. The powder beverage exerted the effect of the present invention.

| | |
|---|---|
| Young barley grass powder | 74% by mass |
| Green tea | 4% by mass |
| Maltitol | 22% by mass |

Example 3

(Production of Cookies)

Cookies consisting of the following ingredients were produced. The cookies exerted the effect of the present invention.

| | |
|---|---|
| Young barley grass powder | 7.41% by mass |
| Wheat powder | 37.04% by mass |
| Butter | 15.43% by mass |
| Sugar | 18.52% by mass |
| Baking powder | 1.54% by mass |
| Egg | 20.06% by mass |

INDUSTRIAL APPLICABILITY

Since the composition of the present invention can be used as health food products, etc., it is industrially applicable.

The invention claimed is:

1. A method for maintaining or improving mucosal immune function, comprising administering a composition comprising young barley grass ground product to a human continuously for 2 weeks or more, in an amount so that the human ingests 0.25 g or more and 10 g or less of the young barley grass ground product per day,
wherein:
    a content of the young barley grass ground product in the composition is 1 to 100% by mass,
    the composition comprises 1 to 70% by mass of dietary fiber derived from young barley grass in terms of dry mass, and
    the composition is a powdered beverage.

* * * * *